United States Patent [19]

Sorodsky

[11] Patent Number: 5,656,268

[45] Date of Patent: Aug. 12, 1997

[54] BIOLOGICAL PRODUCT

[76] Inventor: Michael Sorodsky, 850 W. 176 St. #3c, New York, N.Y. 10033

[21] Appl. No.: 426,042

[22] Filed: Apr. 21, 1995

[51] Int. Cl.$^6$ .................................................. A01N 63/00
[52] U.S. Cl. ......................... 424/93.45; 424/93.44
[58] Field of Search .......................... 424/404, 93.45, 424/93.44

[56] References Cited

U.S. PATENT DOCUMENTS

| | | | |
|---|---|---|---|
| 3,072,528 | 1/1963 | Kludas et al. | 424/93.45 |
| 4,524,136 | 6/1985 | Lee et al. | 435/139 |
| 4,980,164 | 12/1990 | Manfredi et al. | 424/93.45 |
| 5,093,121 | 3/1992 | Kvanta et al. | 424/93.44 |
| 5,135,739 | 8/1992 | Tsurumizu et al. | 424/93.44 |
| 5,190,755 | 3/1993 | Molin et al. | 424/93.45 |

FOREIGN PATENT DOCUMENTS

| | | |
|---|---|---|
| 2852779 | 6/1979 | Germany . |
| 3125797 | 1/1983 | Germany . |
| 47-019192A | 6/1972 | Japan . |
| 58-008018A | 1/1983 | Japan . |
| 2037160 | 7/1980 | United Kingdom . |
| 2072502 | 8/1991 | United Kingdom . |

*Primary Examiner*—Thurman K. Page
*Assistant Examiner*—Sharon Howard
*Attorney, Agent, or Firm*—Kirschstein, Ottinger, Israel & Schiffmiller, P.C.

[57] ABSTRACT

A biological product comprises a milk ingredient and bacteria including bacterium ferments, bolgarium bacillus, acedofilium bacillius, lactobacterium gelveticum, termofilium streptococum, bacterium kazey.

9 Claims, No Drawings

BIOLOGICAL PRODUCT

BACKGROUND OF THE INVENTION

The present invention relates generally to a biological product.

Biological products usually include milk or milk products, bacteria and oil. Some of these products are disclosed in U.S. Pat. Nos. 4,524,136, 4,565,698, 4,877,615, 5,086,040, 5,324,515, and 4,942,032. These products can be further improved.

SUMMARY OF THE INVENTION

Accordingly, it is an object of the present invention to provide a biological product which is a further improvement of the existing products.

In keeping with these objects and with others which will become apparent hereinafter, one feature of the present invention resides, briefly stated, in a biological product, comprising a milk ingredient, and at least two bacteria selected from the group consisting of ferments or cultures of *Lactobacillus bulgaricum, Lactobacillus acidophilus, Lactobacillus helveticus, Lactobacillus casei* and *Streptococcus thermophilus*.

In accordance with the present invention the milk ingredient can be pure milk or an ingredient produced from milk.

In accordance with still a further modification of the present invention the biological product can include oil, such as olive oil, vegetable oil and aromatic oil.

The novel features which are considered as characteristic for the invention are set forth in particular in the appended claims. The invention itself, however, both as to its composition and its method of operation, together with additional objects and advantages thereof, will be best understood from the following description of specific embodiments.

DESCRIPTION OF THE PREFERRED EMBODIMENTS

The new biological product in accordance with the present invention includes a milk ingredient and bacteria including ferments or cultures of *Lactobacillus bulgaricum, Lactobacillus acidophilus, Lactobacillus helveticus, Lactobacillus casei* and *Streptococcus thermophilus*.

The milk ingredient can be 100% pure milk, an ingredient produced from milk, or a mixture of milk ingredients.

In accordance with the invention an oil is also included in the product. It can be 100% pure olive oil, vegetable oil, or aromatic oil (aroma oil). In addition, plant food admixtures can be added, such as fruits, vegetables, flowers, grass, as well as honey and ferments.

The basic composition of the biological product includes the milk ingredient and the bacteria.

The biological product in accordance with the present invention is produced in the following way:

Milk, milk ingredients, or milk whey are mixed with bacteria in equal or unequal parts and are subjected to thermostating at temperature of 42° C. during several hours until a homogenous mixture is obtained with acidity of 100°–600° T (Turner). The quantity of bacteria is $9-12.10^6$ in accordance with the scale of Goreev. Usually, each of five cultures is fermented on pure milk so as to obtain culture in fermented condition. Then the fermented portions are added to the milk, or to whey, or whipped cream, etc. in the quantity of 5%–10% of the whole mass. After the fermentation and obtaining a homogeneous acidity in accordance with the Turner scale, the product can be used.

The product described hereinabove is a basic product. It can be used for several applications.

In order to produce a cosmetic cream, the pure whipped cream with the five bacteria specified hereinabove, are subjected to thermostating. 5%–10% of prepared bacterial fermented portions on milk are added into the whipped cream or sour cream and then subjected to thermostating at a temperature 42° C. until the acidity of 100°–600° T is obtained depending on the required cream. Then the cream is aromatized by addition of 100% natural aroma oils. Also, plant oil can be added such as for example olive oil in the quantity of 1–15% depending on the oiliness of the face skin. Vegetables or fruits, such as avocado, cucumber, strawberry, etc. can be added. The whole mass is whipped and can be stored in the refrigerator at temperatures above 0° C.

In order to produce creams and liquids for body and massage, at least two of five components specified hereinabove are fermented on milk ingredient until acidity of 300°–600° T is obtained. Then the mass is whipped, and whipped fruits, juices, syrups are added.

In order to produce a cream for gum treatment, as well as for taking internally, at least two of five components specified hereinabove are combined with whipped cream or sour cream to obtain acidity up to 400° T.

For medical applications the product is made on milk whey or milk, or other milk product, and depending on the corresponding application brought to a required acidity. Then it is used either as a drink or as cream.

Finally, dry sublimed biological product can be introduced into food products as an additive for improving user's health. Pills can be made as well.

It also can be used in spa for taking baths.

It will be understood that each of the elements described above, or two or more together, may also find a useful application in other types of products differing from the types described above.

While the invention has been illustrated and described as embodied in a biological product, it is not intended to be limited to the details shown, since various modifications and compositional changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A biological product in liquid or cream form comprising pure milk or a milk ingredient and the ferments or cultures of bacterial species *Lactobacillus fermentum, Lactobacillus bulgaricum, Lactobacillus acidophilus, Lactobacillus helveticus, Lactobacillus casei* and *Streptococcus thermophilus*.

2. A product according to claim 1 which comprises a milk ingredient selected from the group consisting of whey, cream, whipped cream or sour cream.

3. A product according to claim 1 in the form of a homogenous mixture having an acidity of about 100°–600° T.

4. A product according to claim 1 which further comprises an oil selected from the group consisting of olive oil, vegetable oils and aromatic oils.

5. A product according to claim 1 which further comprises a food or plant admixture derived from fruits, vegetables, flowers, grasses or honey.

6. A biological product comprising ferments or cultures of at least two bacterial species selected from the group consisting of *Lactobacillus bulgaricum, Lactobacillus acidophilus, Lactobacillus helveticus, Lactobacillus casei* and *Streptococcus thermophilus*.

7. A product according to claim 6 comprising ferments or cultures of all the bacterial species *Lactobacillus bulgaricum, Lactobacillus acidophilus, Lactobacillus helveticus, Lactobacillus casei* and *Streptococcus thermophilus*.

8. A product according to claim 6 in dry or sublimed form.

9. A product according to claim 7 in dry or sublimed form.

* * * * *